US00PP31887P3

(12) United States Plant Patent
Jamieson

(10) Patent No.: US PP31,887 P3
(45) Date of Patent: Jun. 16, 2020

(54) ***AGAPANTHUS* PLANT NAMED 'SHONA'**

(50) Latin Name: *Agapanthus praecox*
Varietal Denomination: Shona

(71) Applicant: THE CONARD-PYLE COMPANY, West Grove, PA (US)

(72) Inventor: Richard Jamieson, Kirstenhof (ZA)

( * ) Notice: Subject to any disclaimer, the term of this patent is extended or adjusted under 35 U.S.C. 154(b) by 0 days.

(21) Appl. No.: 16/350,048

(22) Filed: Sep. 20, 2018

(65) Prior Publication Data

US 2019/0110387 P1 Apr. 11, 2019

Related U.S. Application Data

(60) Provisional application No. 62/606,743, filed on Oct. 6, 2017.

(51) Int. Cl.

| | |
|---|---|
| ***A01H 6/00*** | (2018.01) |
| ***A01H 5/02*** | (2018.01) |
| ***A01H 6/56*** | (2018.01) |

(52) U.S. Cl.
USPC ..... Plt./398
CPC ..... *A01H 6/56* (2018.05)

(58) Field of Classification Search
USPC ..... Plt./398
CPC ..... A01H 5/02; A01H 6/56; A01H 6/00
See application file for complete search history.

(56) References Cited

U.S. PATENT DOCUMENTS

PP25,557 P2 5/2015 Jamieson

*Primary Examiner* — Keith O. Robinson
(74) *Attorney, Agent, or Firm* — Panitch Schwarze Belisario & Nadel LLP

(57) ABSTRACT

A new and distinct variety of *Agapanthus* plant, herein referred to by its cultivar name, 'Shona', is provided which forms on a substantially continuous basis attractive white colored flowers. Attractive, medium green-colored evergreen foliage is formed. The growth habit is moderately vigorous and compact upright-mounded. The new variety is well suited for providing attractive ornamentation in the landscape.

2 Drawing Sheets

Figure 1:
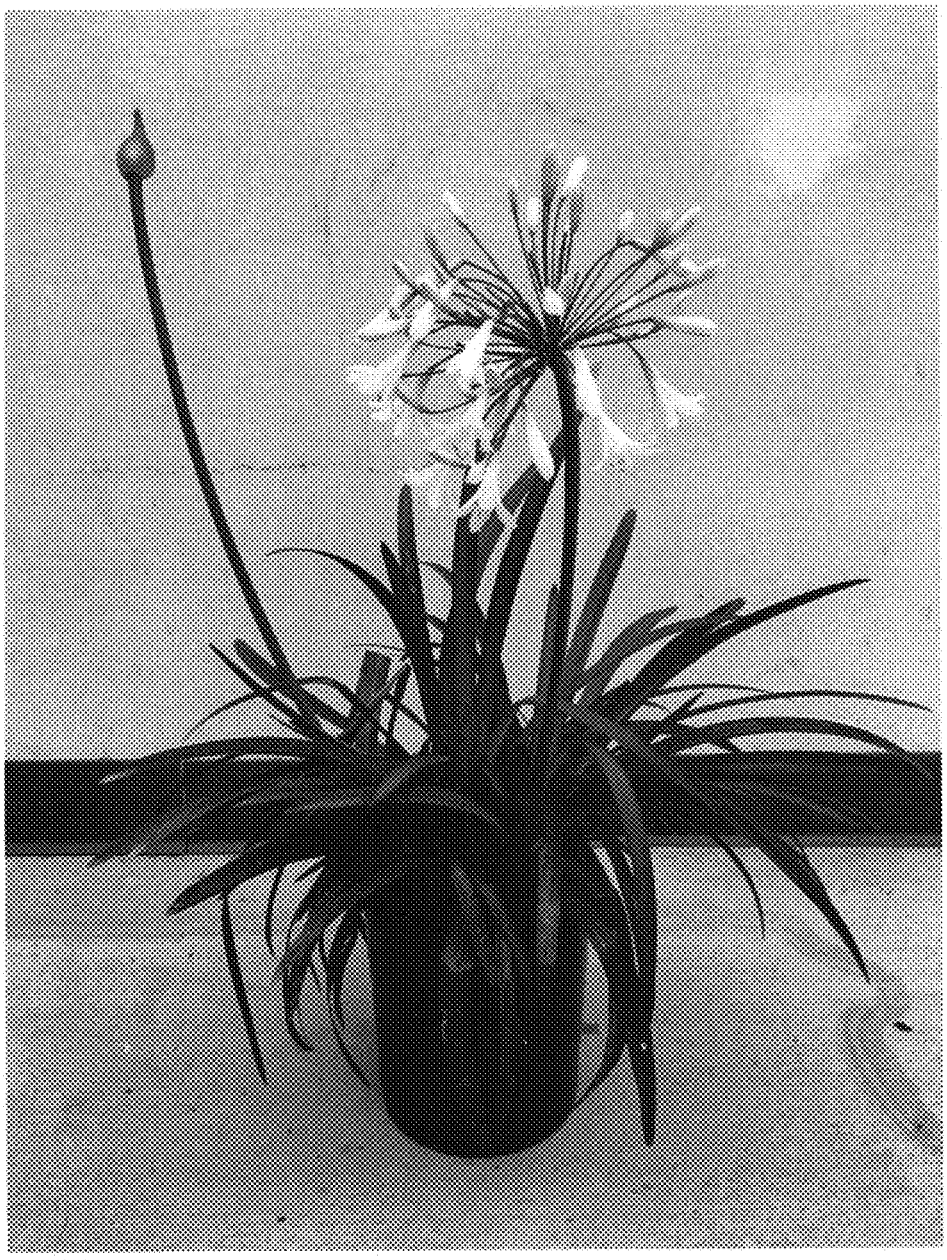

Botanical/commercial classification:
Latin name: *Agapanthus praecox.*
Varietal denomination: 'Shona'.

SUMMARY OF THE INVENTION

The new variety of *Agapanthus praecox* plant originated in a controlled breeding program in Cape Town, Republic of South Africa during October, 2011. The objective of the breeding program was the development of *Agapanthus* cultivars with earlier flowering and improved self-cleaning. The new cultivar was the result of open-pollination. The female parent (i.e., the seed parent) was the 'Double Diamond' variety (non-patented). The male parent (i.e., the pollen parent) is unknown.

The parentage of the new variety can be summarized as follows:

'Double Diamond' x unknown

The new cultivar was discovered and selected as a single flowering plant from the progeny resulting from the above stated open-pollination during October 2013 in a controlled environment in Cape Town, Republic of South Africa. Selective study resulted in the identification of a single plant of the new variety.

It was found that the new variety of *Agapanthus* plant of the present invention:

(a) substantially continuously forms white colored flowers,
(b) displays medium green-colored evergreen foliage, (c) exhibits a moderately vigorous and compact upright-mounded growth habit,
(d) produces early blooming, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Double Diamond' variety (i.e., the seed parent) displays double inflorescences, whereas the new variety displays single flowers and exhibits longer flowering stem length and blooming earlier in the season than the 'Double Diamond' variety.

The new variety can also be distinguished from other similar varieties that are commercially available. For instance, the new variety of the present invention can readily be distinguished from the 'Jonie' variety (U.S. Plant Pat. No. 25,557), as the new cultivar is earlier to bloom and displays a shorter foliage canopy than the 'Jonie' variety. Additionally, the 'Jonie' variety displays blue-purple colored flowers, whereas the new variety displays white colored flowers.

The new variety has been found to undergo asexual reproduction by a number of routes, including in vitro propagation. Asexual propagation by the above-mentioned techniques in Cape Town, Republic of South Africa since October, 2014 has shown that the characteristics of the new variety are stable and are strictly transmissible by such asexual propagation from one generation to another. Accordingly, the new variety undergoes asexual propagation in a true-to-type manner.

The new variety has been named 'Shona'.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Shona' variety. The plants were grown in one-gallon containers for approximately 12 months in an outdoor nursery in Arroyo Grande, Calif. In late November, 2017, the plants were transferred to West Grove, Pa. and held under greenhouse conditions to flower.

FIG. 1—illustrates a specimen of the plant displaying the overall growth and flowering habit—side view.

Figure 2:
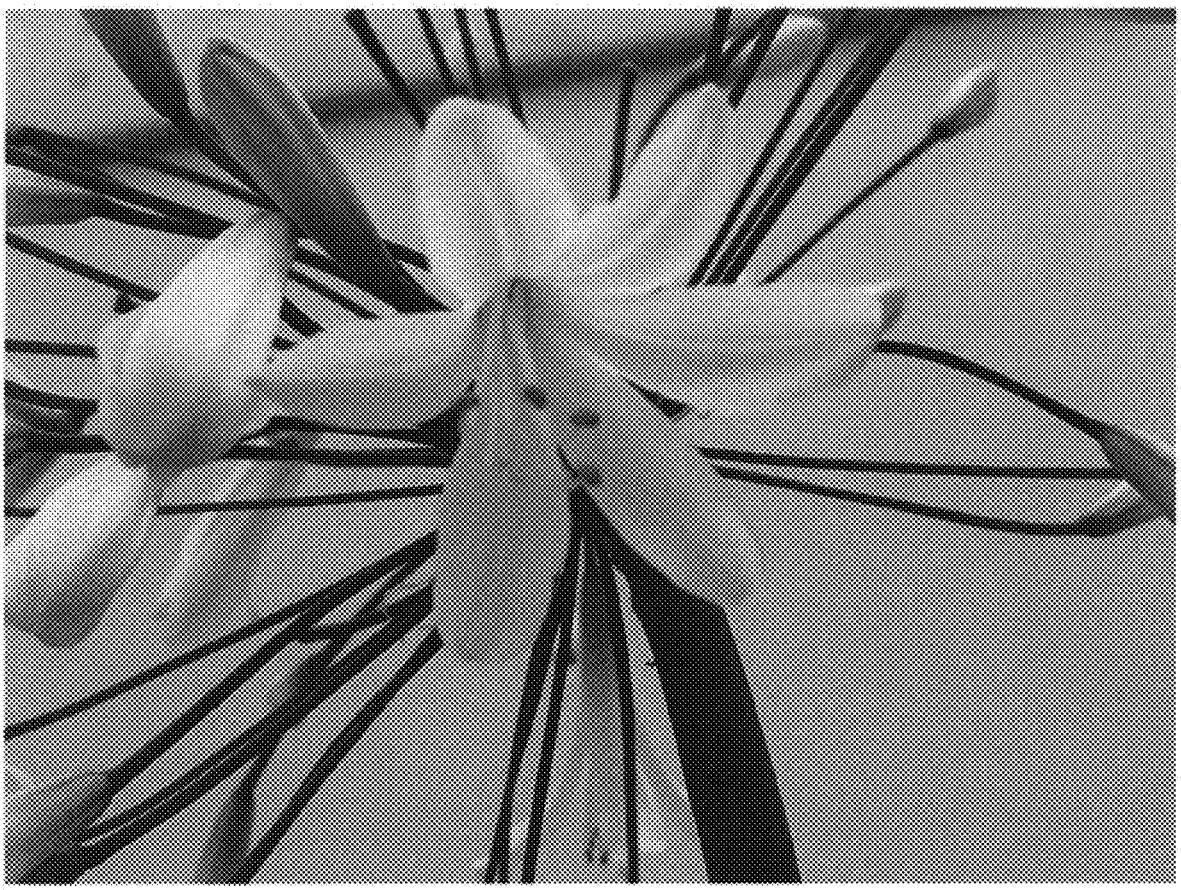

FIG. 2—illustrates a specimen of a flower in the course of opening.

DETAILED BOTANICAL DESCRIPTION

The chart used in the identification of the colors is that of The Royal Horticultural Society (R.H.S. Color Chart), 2015 edition, London, England. The terminology which precedes reference to the chart has been added to indicate the corresponding color in more common terms. The color values were determined in December, 2017 under natural light conditions in West Grove, Pa. The description is based on the observation of plants produced by division of stock plants and grown in a glass-covered greenhouse. The plants were grown in one-gallon containers utilizing a soilless growth medium. Greenhouse temperatures were maintained at 74° F. to 80° F. (23° C. to 27° C.) during the day and approximately 66° F. to 70° F. (19° C. to 21° C.) during the night. Greenhouse light levels of 2,100 footcandles to 4,122 footcandles were maintained during the day.

Class: *Agapanthus* Plant.

Propagation:

*Type cutting*.—Division, perennial bulb.

*Root description*.—Thick and fleshy.

*Rooting habit*.—Freely branching.

Plant:

*Habit*.—Moderate growth vigor, upright-mounded, clumps of arching leaves and flowering stalks.

*Type*.—Evergreen.

*Commercial crop time*.—Approximately 6 to 9 months from a division to finish in a one-gallon container.

*Cold hardiness*.—Commonly to USDA Zone 7.

*Size*.—Approximately 46.0 cm in height from soil level to top of plant plane on average; approximately 33.0 cm in height from soil level to top of foliage; and approximately 60.0 cm in width on average.

Branches:

*Branching habit*.—No branching, basal rosettes of leaves.

*Number of clumps per pot*.—Approximately 4 on average.

*Number of rosettes per clump*.—Approximately 2 or 3 on average.

Foliage:

*Number of leaves*.—Approximately 10 per rosette on average.

*Fragrance*.—None detected.

*Form*.—Simple.

*Arrangement*.—Opposite.

*Density*.—Medium.

Leaves:

*Shape*.—General: lorate. — aspect: emerging leaves erect, then cascade. — margin: entire. — apex: acute. — base: sessile, sheathed.

*Venation pattern*.—Parallel.

*Size*.—Length of mature leaf: approximately 27.0 cm on average. — width of mature leaf: approximately 2.0 cm on average.

*Texture*.—Upper and lower surfaces: glabrous.

*Color*.—Variegation: absent. upper and lower surfaces of young foliage: commonly near Yellow-Green Group 144A and venation is commonly near Yellow-Green Group 146B. — upper surface of mature foliage: commonly near Green Group 136B and venation is commonly near Green Group 136A. — lower surface of mature foliage: commonly near Green Group 138A and venation is commonly near Green Group NN137A.

Inflorescence:

*Quantity*.—Approximately 1 fully open umbel per plant, approximately 1 developing umbel per plant, and approximately 10 fully open flowers per inflorescence.

*Type*.—Umbel, self-cleaning; positioned above foliage.

*Fragrance*.—None detected.

*Length or height*.—Approximately 14.0 cm on average.

*Width*.—Approximately 20.0 cm on average.

*Shape of the lateral view*.—Circular.

*Bract*.—Opening one side.

*Scape*.—Strength: strong. — aspect: erect to 45° angle. — shape in cross-section: cylindrical, pithy center. — length: approximately 38.0 cm on average. — diameter: approximately 1.0 cm on average. — texture: glabrous. — color: commonly near Green Group 137C.

*Peduncle*.—Length: approximately 35.0 cm on average. — diameter: approximately 1.5 cm on average. — strength: very strong. — color: commonly near Green Group 137C. — texture: glabrous. — aspect: erect.

Flower:

*Type*.—Single.

*Shape*.—Funnelform, flared.

*Size*.—Diameter is approximately 4.4 cm on average and depth is approximately 4.3 cm on average.

*Rate of opening*.—Approximately 3 to 4 days for bud to progress from first color to fully open flower.

*Bud just before opening*.—Shape: obovate. — length: approximately 4.3 cm on average. — width: approximately 1.2 cm on average. — texture: glabrous. — color: commonly near NN155C.

*Tepals*.—Quantity: commonly 6. — appearance: dull. — shape: oblanceolate. — margin: entire. — apex: acute. — base: fused. — length: approximately 4.3 cm on average. — width: approximately 6.0 mm on average. — texture of upper and lower surfaces: glabrous. — color of upper surface when first and fully open: commonly near White Group NN155C. — color of lower surface when first and fully open: commonly near White Group NN155C. — tepal-like staminodes and pistillodes: present.

*Perianth*.—Length: approximately 3.5 cm on average. — diameter: approximately 4.0 cm on average.

*Perianth tube*.—Length: approximately 4.3 cm on average. — width: approximately 1.2 cm on average. — texture: glabrous. — color: commonly near White Group NN155C.

*Pedicles*.—Strength: strong. — aspect: acute angle to horizontal. — length: approximately 5.1 cm on average. — diameter: approximately 1.0 mm on average. — texture: glabrous. — color: commonly near Green Group 143A.

*Reproductive organs*.—Androecium. — quantity: commonly 6 per flower, adnate to corolla tube. — extrusions of the stamens: absent. — anther: shape is oblong, dorsifixed; length is approximately 2.5 mm on average; and coloration is commonly near Yellow Group 9A. — filament: color is commonly near White Group NN155B. — pollen: amount is moderate and coloration is commonly near Yellow Group 9A. — gynoecium: — pistil: commonly 1 per flower and length is approximately 4.3 mm on average. — stigma: shape is undifferentiated. — style: length is approximately 3.6 cm on average and coloration is commonly near White Group NN155C. — ovary: length is approximately 0.7 mm on average and coloration is commonly near Yellow-Green Group 145A. — seed and fruit: none have been observed to date.

Development:

*Blooming*.—Freely flowering under outdoor growing conditions with substantially continuous blooming from spring through summer.

*Lastingness of individual flower*.—Approximately one to two weeks.

*Tolerance to disease*.—Is not available at this stage.

The new 'Shona' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Agapanthus* plant characterized by the following combination of characteristics:

(a) substantially continuously forms white colored flowers, (b) displays medium green-colored evergreen foliage, (c) exhibits a moderately vigorous and compact upright-mounded growth habit, (d) produces early blooming, and (e) is well suited for providing attractive ornamentation; substantially as herein shown and described.

* * * * *